United States Patent [19]
Wolfers et al.

[11] 4,145,507
[45] Mar. 20, 1979

[54] REACTION MIXTURES, PROCESSES FOR THEIR PREPARATION AND THEIR USE AS POLYMERIZATION INITIATORS

[75] Inventors: Heinrich Wolfers, Rheurdt; Hans Rudolph; Hans J. Rosenkranz, both of Krefeld, all of Fed. Rep. of Germany

[73] Assignee: Bayer Aktiengesellschaft, Fed. Rep. of Germany

[21] Appl. No.: 815,159

[22] Filed: Jul. 13, 1977

[30] Foreign Application Priority Data

Jul. 17, 1976 [DE] Fed. Rep. of Germany ....... 2632294
Dec. 15, 1976 [DE] Fed. Rep. of Germany ....... 2656782

[51] Int. Cl.$^2$ .............................................. C08G 77/04
[52] U.S. Cl. ................. 528/25; 260/448.2 E; 260/448.8 R; 526/194; 528/10; 528/33; 528/42; 528/43

[58] Field of Search .................. 260/46.5 R, 448.2 E, 260/448.8 R; 528/10, 25, 33, 42, 43

[56] References Cited

U.S. PATENT DOCUMENTS

| 2,559,342 | 7/1951 | Burkhard | 260/448.8 |
| 3,048,499 | 8/1962 | Jellinek | 260/46.5 R |
| 3,078,184 | 2/1963 | Ender | 260/46.5 R |
| 3,287,291 | 11/1966 | Ender | 260/46.5 R |
| 3,981,898 | 9/1976 | Lohse et al. | 260/448.8 R |

Primary Examiner—Melvyn I. Marquis
Attorney, Agent, or Firm—Connolly and Hutz

[57] ABSTRACT

Mixtures obtained by reaction of an α-arylketone or of an arylaldehyde and the equivalent amount of a base metal in an inert aprotic solvent with a di-, tri- or tetrachlorosilane or a chlorinated polyorganosilane or -siloxane work as initiators for free radical-initiated polymerization reactions.

3 Claims, No Drawings

REACTION MIXTURES, PROCESSES FOR THEIR PREPARATION AND THEIR USE AS POLYMERIZATION INITIATORS

The present invention relates to reaction mixtures which are obtainable by reacting base metals with α-arylketones or arylaldehydes and di-, tri- or tetrachloro-organosilanes, chlorinated polyorganosilanes or siloxanes, a process for their preparation and their use as initiators for polymerisation reactions which can be initiated by free radical mechanisms. The invention also relates to the active ingredients of the reaction mixture, namely a series of oligomeric silyl ethers.

It is known from DT-AS (German Published Specifications) Nos. 1,216,877 and 1,219,224 and from DT-OS (German Published Specifications) Nos. 2,131,623 and 2,164,482 that 1,1,2,2-tetraaryl-1,2-dihydroxyethanes and their alkyl and silyl ethers are suitable as initiators for polymerisation reactions which proceed by free radical mechanisms. In contrast to the known peroxide catalysts, these substances can be handled without any danger. In the presence of these initiators, the curing of substances which can be polymerised by free radical mechanisms can be easily and reliably regulated by simple temperature control.

The object of the present invention is to provide substances which are suitable as initiators for polymerisation reactions which proceed by free radical mechanisms, wherein the initiating action of these substances is not based on the reaction possibilities of the peroxide grouping. The desired substances should also have good storage stability in the polymerisable systems at room temperature but at higher temperatures their reactivity, at concentrations which are as low as possible in the polymerisable system, should exceed that of the peroxide-free initiators already known.

Surprisingly, it has now been found that the reaction of base metals, preferably of metals of the 1st and 2nd principal groups in the periodic table, and especially of lithium, sodium, potassium, magnesium or calcium, as well as aluminium, with α-arylketones or arylaldehydes and di-, tri- or tetra-chloro-organosilanes, chlorinated polyorganosilanes or -siloxanes in an inert solvent readily leads, in very high yield, to reaction mixtures which, even in low concentrations and in some cases already at temperatures above 40° C., effect rapid and complete hardening of the substances to be polymerised. Thus, according to the invention, a process for the preparation of a reaction mixture suitable as an initiator for free radical-initiated polymerisation reactions, which comprises reacting 1 mol of an α-arylketone or of an arylaldehyde of the general formula V or VI respectively $$R^4-\underset{\underset{O}{\|}}{C}-R^6 \quad (V) \quad R^4-CHO \quad (VI)$$

wherein $R^4$ represents an aryl radical optionally substituted by $C_1-C_4$ alkyl, methoxy, chlorine or fluorine, and $R_6$ represents an aryl radical optionally substituted by $C_1-C_4$ alkyl, methoxy, chlorine or fluorine, or a $C_1-C_6$-alkyl radical optionally substituted by $C_1-C_4$ alkyl, methoxy, chlorine or fluorine, or a $C_5-C_7$-cycloalkyl radical or hydrogen and approximately the equivalent amount of a base material in an inert aprotic solvent at −10 to +70° C. with 0.4 to 0.8 mol of a dichloro-organosilane of the general formula VII $$R^1R^{2'}SiCl_2 \quad (VII)$$

or with 0.25 to 0.6 mol of a trichloro-organosilane of the general formula VIII $$R^1SiCl_3 \quad (VIII)$$

wherein $R^1$ represents a methyl, ethyl, phenyl, benzyl or chloromethyl radical, and $R^2$ represents a chlorine atom, a hydroxyl, methoxy or ethoxy radical, or one of the substituents $R^1$ or with 0.1 to 0.7 mol of tetrachlorosilane, chlorinated polyorganosilanes or -siloxanes having a molecular weight of 150 to 3000, until the exothermix reaction has ended, hydrolysing the reaction product, separating off the organic phase and stripping off the solvent under a pressure of between 2 and 6 mm Hg.

The systems capable of polymerisation which contain the initiating reaction mixtures according to the invention are distinguished by a relatively high storage stability. A further advantage of the initiators according to the invention is that, on decomposition into radicals, they do not liberate any volatile substances which can cause undesirable blister formation in the polymer. The active part of these reaction mixtures, in so far as their polymerisation-initiating function is concerned, is a series of oligomeric silyl ethers with a molecular weight, determined as a number-average, of 500 to 5,000 and preferably of 800 to 2,500, of the general formula I

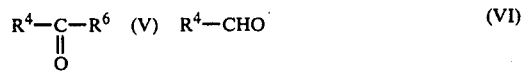

wherein $R^1$ denotes a methyl, ethyl, phenyl, benzyl or chloromethyl radical, $R^2$ denotes a chlorine atom, a hydroxyl, methoxy or ethoxy radical, $R^1$ or A $R^3$ denotes a chlorine atom, a hydroxyl radical or A, $R^4$ and $R^5$ each denote an aryl radical optionally substituted by $C_1-C_4$-alkyl (preferably methyl), methoxy, chlorine or fluorine (preferably phenyl, tolyl, p-tert.-butyl-phenyl, o- or p-chlorophenyl, 2,4-dichlorophenyl, naphthyl, biphenylyl or m-methoxyphenyl), $R^6$ and $R^7$ each denote either $R^4$ or $R^5$ or an alkyl radical with 1-6 C-atoms which is optionally substituted by $C_1-C_4$-alkyl (preferably methyl), methoxy, chlorine or fluorine (preferably methyl, ethyl or isopropyl), or a cycloalkyl radical with 5-7 C-atoms (preferably cyclohexyl) or hydrogen, $R^8$ denotes hydrogen or a silyl radical of the general formula II $$\underset{\underset{R^2}{|}}{\overset{\overset{R^1}{|}}{-Si}}-A \quad (II)$$

and A denotes a radical of the general formula III

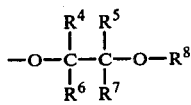

the compounds of the general formula I containing one to twenty partial structures IV

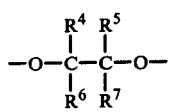

Preferably the base metal comprises about 0.5 mol of a metal of the 2nd principal group of the periodic table, such as magnesium or calcium, or about 1 mol of a metal of the 1st principal group of the periodic table, such as lithium, sodium or potassium, or about ⅓ mole of a metal of the 3rd principal group of the periodic table, such as aluminium. The reaction in the inert aprotic solvent preferably takes place at −5 to + 50° C., with cooling if necessary, and there is preferably used 0.5 to 0.6 mol of a dichloro-organosilane of the formula VII or 0.3 to 0.4 mol of a trichloro-organosilane of the formula VIII, or with 0.2 to 0.5 mol of a tetrachloro-silane or of a (preferably 2 to 6) chlorine atoms containing polyorganosilane or -siloxane having a molecular weight of 150 to 1500.

The solvent is suitably stripped off at 20° C.

The invention also comprises reaction mixtures obtainable by the process of the invention, together with the use of the reaction mixtures according to the invention and of the silylethers of general formula I as initiators for polymerisation reactions which can be initiated by free radical mechanisms.

The oligomeric silyl ethers prepared from tetrachlorosilanes, chlorinated polyorganosilanes or -siloxanes have an average number molecular weight of 500 to 12,000, preferably 2000 to 8000 and contain one to twenty structures IV.

The chlorine atoms containing polyorganosilanes and -siloxanes to be used as starting materials according to the invention may contain 2 to 20 silicon atoms; the valences not saturated with silicium, chlorine and siloxy generally bear aliphatic, cycloaliphatic or aromatic radicals having 1 to 20, preferably 1 to 6, carbon atoms, preferably methyl, ethyl or phenyl.

The molecular weight of the silyl ethers according to the invention is determined by vapour pressure osmometry up to a molecular weight of 3,000 and by membrane osmometry for a molecular weight above 3,000, the determinations being carried out in acetone as the solvent in each case. The molecular weights of individual fractions of the reaction mixtures according to the invention can be determined by gel chromatography (by means of standard substances).

Various reactants are listed below as examples of the base metals, aldehydes or ketones and silanes to be employed as starting materials:

| | | | |
|---|---|---|---|
| 1) | magnesium | benzaldehyde | trichloromethylsilane |
| 2) | magnesium | benzaldehyde | trichlorophenylsilane |
| 3) | magnesium | benzaldehyde | dichlorodimethylsilane |
| 4) | magnesium | acetophenone | trichloromethylsilane |
| 5) | sodium | acetophenone | diphenyldichlorosilane |
| 6) | magnesium | propiophenone | trichloromethylsilane |
| 7) | lithium | isopropyl phenyl ketone | trichloromethylsilane |
| 8) | magnesium | cyclohexyl phenyl ketone | trichloromethylsilane |
| 9) | magnesium | benzophenone | trichloromethylsilane |
| 10) | magnesium | benzophenone | dichlorodimethylsilane |
| 11) | sodium | benzophenone | trichlorophenylsilane |
| 12) | lithium | 4,4-dimethylbenzophenone | trichloromethylsilane |
| 13) | potassium | benzophenone | dichlorodiphenylsilane |
| 14) | calcium | 4-t-butylbenzophenone | trichloromethylsilane |
| 15) | magnesium | 4-chlorobenzophenone | trichloromethylsilane |
| 16) | sodium | 2-methylbenzophenone | dichlorodimethylsilane |
| 17) | magnesium | 2-chlorobenzophenone | trichloromethylsilane |
| 18) | magnesium | 2,4-dichlorobenzophenone | trichloroethylsilane |
| 19) | magnesium | 3-methoxybenzophenone | dichloroethoxymethyl- silane |
| 20) | magnesium | naphthyl phenyl ketone | trichloromethylsilane |
| 21) | magnesium | 4-phenylbenzophenone | trichloromethylsilane |
| 22) | magnesium | 4-benzoylbenzophenone | trichloromethylsilane |
| 23) | magnesium | benzaldehyde | tetrachlorosilane |
| 24) | aluminium | acetophenone | 1.2-dichloro-tetramethyl- disilane |
| 25) | magnesium | acetophenone | tetrachlorosilane |
| 26) | aluminium | isopropyl phenyl ketone | $\begin{array}{c}\phantom{x}\\ Cl-\underset{\underset{CH_3}{|}}{\overset{\overset{CH_3}{|}}{Si}}-\left(O-\underset{\underset{CH_3}{|}}{\overset{\overset{CH_3}{|}}{Si}}\right)_2-O-\underset{\underset{CH_3}{|}}{\overset{\overset{CH_3}{|}}{Si}}-Cl\end{array}$ |
| 27) | magnesium | benzophenone | tetrachlorosilane |
| 28) | magnesium | benzophenone | 1.1.2-trichlorotrimethyl- disilane |
| 29) | aluminium | benzophenone | $CH_3-Si\left(-O-\underset{\underset{CH_3}{|}}{\overset{\overset{CH_3}{|}}{Si}}-O-\underset{\underset{CH_3}{|}}{\overset{\overset{CH_3}{|}}{Si}}-Cl\right)_3$ |
| 30) | sodium | 2-chlorobenzo- phenone | $Cl-\underset{\underset{CH_3}{|}}{\overset{\overset{CH_3}{|}}{Si}}-\left(O-\underset{\underset{CH_3}{|}}{\overset{\overset{CH_3}{|}}{Si}}\right)_{5-6}-O-\underset{\underset{CH_3}{|}}{\overset{\overset{CH_3}{|}}{Si}}-Cl$ |
| 31) | magnesium | 3-methoxybenzo- phenone | 1.2.3.4-tetrachloro- hexamethyl tetrasilane |

-continued

| 32) | lithium | 4-tert.-butyl benzophenone | $\text{Si}\left(\text{O}-\underset{\underset{CH_3}{|}}{\overset{\overset{CH_3}{|}}{\text{Si}}}-\text{O}-\underset{\underset{CH_3}{|}}{\overset{\overset{CH_3}{|}}{\text{Si}}}-\text{Cl}\right)_4$ |
|---|---|---|---|

Examples of inert aprotic solvents are aromatic compounds and alkyl-aromatic compounds, such as benzene and toluene, ethers, such as diethyl ether, diisopropyl ether, dibutyl ether, anisole, tetrahydrofuron, dioxane and 1,2-dimethoxyethane, trialkyl phosphates, such as triethyl phosphates and tributyl phosphate, and N,N-disubstituted amides, such as dimethylformamide, N,N-dimethylacetamide and phosphoric acid tris-(dimethylamide). Further suitable solvents are described in Methoden der Organischen Chemie (Methods of Organic Chemistry) (Houben-Weyl), Volume XIII/2 a, page 59–70, Georg Thieme-Verlag, Stuttgart 1973. Solvent mixtures of 0–80 parts by weight of benzene or toluene, 2–98 parts by weight of tetrahydrofurane and 2–98 parts by weight of triethyl phosphate or phosphoric acid tris-(dimethylamide) have proved particularly suitable. In order to avoid unnecessary dilution of the reaction mixture, as little solvent as possible is generally employed. As a rule, a keto compound/solvent weight ratio of 1:1 is completely adequate.

It is advisable to take into account the fact that in some cases decomposition is possible under the reaction conditions. Thus, if the reaction mixture according to the invention should display lower reactivity, which is due to decomposition, during preparation, of the compound which acts as the initiator, it is advisable to lower the reaction temperature.

The reaction mixtures according to the invention are distinguished by high reactivity. Thus, their reactivity is considerably superior to that of the monomeric benzpinacol derivatives.

Some of the reaction mixtures according to the invention are already effective at temperatures above 40° C. Complete and rapid through-curing is as a rule achieved when 0.02 to 1, and preferably 0.05 to 0.8%, by weight, relative to the substance to be polymerised, is employed.

The polymerisation reaction is started by heating a mixture of the substance to be polymerised and the reaction mixture according to the invention above a definite start temperature which is easy to determine for a particular case. Curing or hardening of systems which can be polymerised by free radical mechanisms is as a rule effected at between 60° and 200° C.

Curing can be effected in a single stage but can also be carried out stepwise if desired (compare British Pat. No. 1,041,641).

It is possible to determine the start temperature of the initiator reaction mixture according to the invention by a simple colour reaction: this is because the radicals formed on thermal decomposition can decolorise quinoid dyestuffs. In order to carry out the test, a small amount of a quinoid dyestuff, for example methylene blue, thionine or neutral red, is dissolved in a solvent which is free from molecular oxygen, for example glycol or xylene, and at least the equivalent amount of the reaction mixture according to the invention is added. The temperature at which the dyestuff is decolorised is the start temperature for the initiator reaction mixture.

The start temperature is highly dependent on the structure of the compounds according to formula I.

Initiators containing a large number of bulky (for example aryl) radicals are distinguished (especially in the case of ortho-substituted aryl radicals) by a relatively low start temperature; initiators in which $R^6$ and $R^7$ represent alkyl groups or hydrogen decompose only at higher temperatures and under certain circumstances are still stable up to 80° C. in the substance to be polymerised.

Typical substances in which polymerisation can be initiated by the reaction mixtures according to the invention i.e. all the compounds or mixtures which can be polymerised by free radical mechanisms, include conjugated dienes, such as butadiene, isoprene and chloroprene; vinyl chloride and vinylidene chloride; aromatic vinyl compounds, such as styrene and divinylbenzene; vinyl esters, especially vinyl acetate and vinyl propionate; vinyl esters, such as vinyl propyl ether and vinyl isobutyl ether; acrylic acid and methacrylic acid and their derivatives, such as esters, especially with aliphatic alcohols with 1 to 5 C. atoms, nitriles, amides and the like; di-(vinylphenyl) carbonates; diallyl phthalate, diallyl carbonate and diallyl fumarate; di-(allylphenyl) carbonates; polyol-poly(meth)acrylates; and N,N'methylene-bis-(meth)acrylamide.

Particularly suitable substances in which polymerisation can be initiated by the reaction mixtures according to the invention are unsaturated polyester resins, that is to say the solutions of α,β-ethylenically unsaturated polyesters in monomers which are copolymerisable therewith.

Suitable α,β-ethylenically unsaturated polyesters are the customary polycondensation products of at least one α, β-ethylenically unsaturated dicarboxylic acid with, as a rule, 4 or 5 C. atoms, or the ester-forming derivatives thereof, for example the anhydrides thereof, optionally mixed with up to 200 mol %, relative to the unsaturated acid components, of at least one aliphatic saturated dicarboxylic acid with 4–10 C. atoms or one cycloaliphatic dicarboxylic acid with 8–10 C. atoms, or the ester-forming derivatives thereof, with at least one polyhydroxy compound, especially a dihydroxy compound, with 2–8 C. atoms, that is to say polyesters such as those described by J. Björksten et al., "Polyesters and their Applications", Reinhold Publishing Corp., New York 1956.

Examples of unsaturated dicarboxylic acids, or their derivatives, which are preferably to be used are maleic acid or maleic anhydride and fumaric acid. However, it is also possible to use, for example, mesaconic acid, citraconic acid, itaconic acid or chloromaleic acid. Examples of the aliphatic saturated and cyclo-aliphatic dicarboxylic acids, or their derivatives, which are to be used are phthalic acid or phthalic anhydride, isophthalic acid, terephthalic acid, hexa-or tetra-hydrophthalic acid or their anhydrides, endomethylene-tetrahydrophthalic acid or its anhydride, succinic acid or succinic anhydride and succinic acid esters and succinic acid chlorides, adipic acid and sebacic acid. In order to prepare resins of low flammability it is possible to use, for example, hexachloroendomethylenetetrahydrophthalic acid, tetrachlorophthalic acid or tetrabromophthalic acid. Dihydric alcohols which can be employed are ethylene glycol, propane-1,2-diol, propane-1,3-diol, diethylene glycol, dipropylene glycol, butane-1,3-diol, butane-1,4-diol, neopentyl-glycol, hexane-1,6-diol, 2,2-bis-(4-hydroxycyclohexyl)-propane, bis-oxalkylated bisphenol A, perhydrobisphenol and others. Ethylene glycol, propane-1,2-diol, diethylene glycol and dipropylene glycol are preferably used.

Further modifications are possible by incorporating monohydric, trihydric and tetrahydric alcohols with 1-6 C. atoms, such as methanol, ethanol, butanol, allyl alcohol, benzyl alcohol, cyclohexanol and tetrahydrofurfuryl alcohol, trimethylolpropane, glycerol and pentaerythritol and also mono-, di- and tri-allyl ethers and benzyl ethers of trihydric and polyhydric alcohols with 3-6 C. atoms according to DT-AS (German Published Specification) No. 1,024,654, and also by incorporating monobasic acids, such as benzoic acid, or long-chain unsaturated fatty acids, such as oleic acid, linseed oil fatty acid and castor oil fatty acid.

The acid numbers of the polyesters are usually between 1 and 100 and preferably between 20 and 70, the OH numbers are between 10 and 150 and preferably between 20 and 100 and the molecular weights $\overline{M}_n$, determined as a number-average, are between about 500 and 5,000 and preferably between about 1,000 and 3,000 (measured by vapour pressure osmometry in dioxane and acetone; in the case of differing values, the lower value is regarded as being correct).

Suitable vinyl and vinylidene compounds which can be copolymerised with the unsaturated polyesters are the unsaturated compounds which are customary in polyester technology and preferably carry α-substituted vinyl groups or β-substituted allyl groups, preferably styrene; however, for example, styrenes which are chlorinated and alkylated or alkenylated in the nucleus and in which the alkyl groups can contain 1-4 carbon atoms, for example vinyltoluene, divinylbenzene, α-methylstyrene, tert.-butylstyrene and chlorostyrenes; vinyl esters of carboxylic acids with 2-6 carbon atoms, preferably vinyl acetate; vinylpyridine, vinylnaphthalene, vinylcyclohexane, acrylic acid and methacrylic acid and/or their esters (preferably the vinyl, allyl and methallyl esters) with 1-4 carbon atoms in the alcohol component and their amides and nitriles, maleic anhydride, maleic acid half-esters and diesters with 1-4 carbon atoms in the alcohol component and maleic acid halfamides and diamides, or cyclic imides, such as N-methylmaleimide or N-cyclohexylmaleimide; and allyl compounds such as allylbenzene and allyl esters such as allyl acetate, phthalic acid diallyl ester, isophthalic acid diallyl ester, fumaric acid diallyl ester, allyl carbonates, diallyl carbonates, triallyl phosphate and triallyl cyanurate are also suitable.

The Examples which follow illustrate the invention.

In the test which follows the parts indicated are parts by weight and the percentage data are given as percentages by weight.

EXAMPLE 1

24 g of magnesium and 364 g of benzophenone are initially introduced into a solvent mixture consisting of 500 parts of toluene, 100 parts of phosphoric acid tris-(dimethylamide) and 50 parts of tetrahydrofuran. 110 g of trichloromethylsilane are added slowly dropwise at a temperature of 25-40° C., whereupon the magnesium dissolves completely. After stirring for 4 hours at 30° C., the batch is poured onto 1 liter of ice. The organic phase is washed several times with water and then concentrated at 40° C. under a waterpump vacuum. A highly viscous liquid remains as the residue and after prolonged standing this solidifies to give a glassy solid.

Gel chromatography is carried out using a column combination which separates low-molecular compounds and is filled with Styragel of different pore widths (Waters-Meßtechnik); tetrahydrofurane is employed as the eluate. Benzophenone, acetophenone and benzpinacol are used for standardisation. When correlated with the standard compounds, the following molecular weight distribution is obtained.

| Component | Molecular weight | Percentage surface area |
| --- | --- | --- |
| 1 | 182 | 1.4 |
| 2 | 366 | 5.2 |
| 3 | 520 | 2.3 |
| 4 | 940 | 8.4 |
| 5 | 1,400 | 31.0 |
| 6 | 1,700 | 29.0 |
| 7 | 2,100 | 15.7 |
| 8 | 2,460 | 6.8 |
| $\overline{M}_n$ (osmometry): | 1,400 | |

EXAMPLE 2

Example 1 is modified: 240 g of acetophenone are employed in place of the benzophenone. After working up, a solid resin remains.

Gel chromatography:

| Component | Molecular weight | Percentage surface area |
| --- | --- | --- |
| 1 | 120 | 2.5 |
| 2 | 240 | 1.9 |
| 3 | 700 | 7.5 |
| 4 | 980 | 28.7 |
| 5 | 1,800 | 38.0 |
| 6 | 2,400 | 13.2 |
| 7 | 3,600 | 8.2 |

EXAMPLE 3

23 g of sodium are pressed in filaments into a solvent mixture consisting of 250 ml of absolute tetrahydrofurane and 50 ml of triethyl phosphate. A solution of 196 g of 2-methylbenzophenone and 66 g of dichlorodimethylsilane in 200 cc of absolute tetrahydrofuran are added dropwise to this mixture at −5 to 10° C. When all of the sodium has dissolved, the mixture is stirred for a further 3 hours and the batch is then hydrolysed with 600 g of ice. After washing several times with ice water, the organic phase is placed at 20° C. under a waterpump vacuum.

Gel chromatography:

| Component | Molecular weight | Percentage surface area |
| --- | --- | --- |
| 1 | 450 | 0.8 |
| 2 | 470 | 5.0 |
| 3 | 1,000 | 33.5 |
| 4 | 1,450 | 25.4 |
| 5 | 1,900 | 24.1 |
| 6 | 2,700 | 11.0 |

EXAMPLE 4

An unsaturated polyester prepared from 11 parts of phthalic anhydride, 47 parts of maleic anhydride and 42 parts of propylene 1,2-glycol at 200° C. (acid number 20, OH number 30, viscosity at 20° C.: 1,500 cP) is dissolved in styrene to give a 66% strength solution, the solution is stabilised with 0.01 part of hydroquinone and 0.3 part of one of the initiators 2, 4, 8, 9, 14, 16 and 17 (see the Table hereinabove) or benzpinacol is mixed in in each case. One hour after adding the initiator, 20 g of a resin batch are filled into a test tube 16 mm in diameter. An iron/Konstantan (an alloy of 54% Cu, 45% Ni and 1% Mn) thermoelement, which is connected to a temperature-time recorder, is dipped 3 cm deep into the resin and, after the measuring equipment has been switched on, the test tube, which is filled to a depth of 8 cm, is placed in a thermostat-controlled oil bath. The curing times $t_C$ (time taken to reach the peak temperature less the time which elapses before the 65° C. line is crossed) and the peak temperature ($T_m$) are determined analogously to DIN 16,945.

At the indicated bath temperatures the following values are obtained:

d: 0.75 part of tert.-butylperbenzoate

The resin batches are first thickened for 5 hours at 50° C. and then for 24 hours at room temperature and are subsequently cured, as 7.5 g samples, at 140° C. in a laboratory press. The curing times and the residual styrene content of the polymerised blocks are determined.

| Experiment | Curing time [minutes] | Residual styrene content [%] |
|---|---|---|
| a | 1.41 | 0.8 |
| b | 1.25 | 0.3 |
| c | 1.15 | 0.2 |
| d | 1.40 | 0.4 |

EXAMPLE 7

| Initiator | 2 | | 4 | | 8 | | 9 | | 14 | | 16 | | 17 | | Benzpinacol | |
|---|---|---|---|---|---|---|---|---|---|---|---|---|---|---|---|---|
| | $t_C$ | $T_m$ | $t_C$ | $T_m$ | $t_C$ | $T_m$ | $t_C$ | $T_m$ | $t_C$ | $T_m$ | $t_C$ | $T_m$ | $t_C$ | $T_m$ | $t_C$ | $T_m$ |
| Bath temperature [° C.] | | | | | | | | | | | | | | | | |
| 70 | | | | | | | | | | | | | 14.4 | 160 | | |
| 80 | | | | | | | 14.0 | 190 | 13.0 | 190 | 12.2 | 175 | 9.9 | 195 | | |
| 90 | | | | | | | 9.0 | 220 | 8.6 | 225 | 8.0 | 190 | 6.5 | 210 | | |
| 100 | | | | | 8.8 | 215 | 5.0 | 250 | 4.9 | >250 | 4.6 | 210 | 4.3 | 235 | 12.5 | 225 |
| 110 | | | 7.5 | 220 | 5.8 | 235 | 3.7 | >250 | 3.7 | >250 | 3.2 | 235 | 3.2 | 250 | 7.5 | 240 |
| 120 | 9.0 | 230 | 5.0 | 240 | 4.3 | 250 | 2.8 | >250 | 2.8 | >250 | 2.7 | >250 | 2.8 | >250 | 4.5 | 250 |
| 130 | 6.3 | 245 | 3.8 | 250 | 3.3 | >250 | 2.2 | >250 | 2.2 | >250 | 2.2 | >250 | 2.4 | >250 | 3.6 | >250 |
| 140 | 5.0 | 250 | 3.2 | >250 | 2.8 | >250 | 1.9 | >250 | 1.9 | >250 | 1.9 | >250 | 2.1 | >250 | 3.2 | >250 |

EXAMPLE 5

Example 4 is repeated but the resin batches mixed with initiators 2, 4, 8, 9 and 14 are stored for four days at 60° prior to curing. The measurements subsequently Example 4 is repeated but benzoyl peroxide and mixtures of benzoyl peroxide and initiator 9 are employed as the initiator.

The curing times $t_C$ (minutes) and the maximum temperatures $T_m$ (°C.) are determined.

| Initiator mixture | | Bath temperatures | | | | | | | |
|---|---|---|---|---|---|---|---|---|---|
| Parts of peroxide | Parts of 9 | 80° C. | | 90° C. | | 100° C. | | 110° C. | |
| | | $t_C$ | $T_m$ | $t_C$ | $T_m$ | $t_C$ | $T_m$ | $t_C$ | $T_m$ |
| 0.15 | — | — | — | 10.5 | 225 | 5.5 | 250 | 3.4 | >250 |
| 0.15 | 0.1 | 15 | 210 | 6.0 | 240 | 4.0 | >250 | 2.8 | >250 |
| 0.15 | 0.3 | 10 | 215 | 5.1 | 240 | 3.2 | >250 | 2.2 | >250 |
| 0.25 | — | 15 | 210 | 7.5 | 235 | 4.5 | >250 | 2.8 | >250 |
| 0.25 | 0.1 | 13 | 215 | 4.8 | 245 | 3.5 | >250 | 2.3 | >250 |
| 0.25 | 0.3 | 9 | 225 | 4.0 | >250 | 2.7 | >250 | 1.9 | >250 |
| 0.5 | — | 10 | 220 | 4.8 | 245 | 3.2 | >250 | 2.2 | >250 |
| 0.5 | 0.1 | 8 | 228 | 4.0 | >250 | 2.7 | >250 | 2.0 | >250 |
| 0.5 | 0.3 | 7 | 235 | 3.5 | >250 | 2.3 | >250 | 1.8 | >250 |
| 1.0 | — | 6 | 235 | 3.4 | 250 | 2.6 | >250 | 1.6 | >250 |
| 1.0 | 0.1 | 5 | 243 | 2.3 | >250 | 1.9 | >250 | 1.5 | >250 | carried out showed no changes in the peak temperatures and the curing times.

EXAMPLE 6

An unsaturated polyester resin prepared from 11 parts of phthalic anhydride, 47 parts of maleic anhydride and 42 parts of propylene 1,2-glycol up to 200° C. (acid number 20, OH number 30, viscosity at 20° C.: 1,500 cP) is dissolved in styrene to give a 66% strength solution and the solution is stabilised with 0.01 part of hydroquinone.

100 parts of this resin are mixed with 100 parts of chalk, 4 parts of zinc stearate and, for each experiment, with one of the following initiators:

Experiment a: 0.2 part of initiator 9 (see Table above)
b: 0.4 part of initiator 9
c: 0.8 part of initiator 9

EXAMPLE 8

0.1 part of one of initiators 9 or 10 (see Table above) or benzpinacol is added, in each case, to 33.3% strength solutions of butyl acrylate in toluene and the resulting mixtures are heated, in several 30 g portions, to the indicated temperature. After specific times, samples are taken, 1 ml of a 4% strength solution of hydroquinone in ethyl acetate is added to each sample and the mixture is then poured into an open dish. The solvent is evaporated by heating to 100° C. for 16 hours and the residual monomers are removed by subjecting the residue to a heat treatment at 160° C. in a vacuum drying cabinet (200 mm Hg).

Gravimetric determination of the residues gives the following proportions of polymerised substance [% of the sample weight]:

| polymerisation temperature: 100° C | Polymerisation time [minutes] | | | | |
|---|---|---|---|---|---|
| Initiator | 15 | 30 | 60 | 120 | 240 |
| Benzpinacol | 0 | 16 | 41 | 51 | 87 |
| Initiator 9 | 2 | 35 | 60 | 84 | 96 |
| Initiator 10 | 4 | 28 | 54 | 76 | 91 |

| Polymerisation temperature: 120° C | Polymerisation time [minutes] | | | | |
|---|---|---|---|---|---|
| Initiator | 15 | 30 | 60 | 120 | 240 |
| Benzpinacol | 15 | 33 | 58 | 75 | 96 |
| Initiator 9 | 27 | 48 | 72 | 84 | 99 |
| Initiator 10 | 24 | 42 | 68 | 82 | 97 |

| Polymerisation temperature: 140° C | Polymerisation time [minutes] | | | | |
|---|---|---|---|---|---|
| Initiator | 15 | 30 | 60 | 120 | 240 |
| Benzpinacol | 21 | 38 | 59 | 77 | 97 |
| Initiator 9 | 31 | 60 | 96 | 98 | 99 |
| Initiator 10 | 30 | 62 | 88 | 94 | 99 |

EXAMPLE 9

100 parts of styrene are mixed with 0.2 part of an initiator and the mixture is polymerised at 80° C. or 110° C. in a thermostat-controlled oil bath. The reaction is discontinued after specific times by cooling the solution and the polymerised styrene is precipitated by diluting with five times the volume of methanol.

After 1 hour the polymer is filtered off, washed several times with methanol and then dried overnight at 60° C. in a vacuum drying cabinet.

The following amounts of polymerised styrene are obtained (% of polystyrene).

| Polymerisation temperature: 80° C. | Polymerisation time [minutes] | | | |
|---|---|---|---|---|
| Initiator | 30 | 60 | 120 | 240 |
| Initiator 9 | 0.7 | 3.8 | 10.0 | 17.3 |
| Initiator 10 | 2.5 | 7.0 | 14.0 | 20.2 |
| Benzpinacol | — | — | 0.2 | 0.4 |
| without initiator | — | — | — | — |

| Polymerisation temperature: 110° C. | Polymerisation time [minutes] | | | |
|---|---|---|---|---|
| Initiator | 10 | 15 | 20 | 30 |
| Initiator 4 | 0.3 | 1.4 | 3.4 | 9.6 |
| Initiator 9 | 8.5 | 14.7 | 24.3 | 37.8 |
| Initiator 10 | 8.8 | 15.0 | 22.8 | 34.5 |
| Benzpinacol | 0.9 | 2.8 | 8.9 | 24.8 |
| without initiator | — | — | — | 0.3 |

EXAMPLE 10

24 g of magnesium and 364 g of benzophenone are initially introduced into a solvent mixture of 500 parts of toluene, 100 parts of phosphoric acid tris (dimethyl amide) and 50 parts of tetrahydrofuran. 95 g of tetrachlorosilane are added slowly dropwise at a temperature of 25–40° C., whereupon the magnesium dissolves completely. After stirring for 4 hours at 30° C., the batch is poured onto 1 liter of ice. The organic layer is washed several times with water and then concentrated at 40° C. under a water-jet pump vacuum. The residue is extracted several times with isopropanol of 50° C., dried and analysed by IR spectroscopy and gel chromatography.

Gel chromatography is carried out using a column combination which separates low molecular compounds and is filled with Styragel of different pore diameter (Waters-Mess-technik). Tetrahydrofurane is employed as the eluant. Benzophenone and benzpinacol are used for standardisation. When correlated with the standard compounds, the following molecular weight distribution is obtained.

| Component | molecular weight | percentage surface area |
|---|---|---|
| 1 | ca. 350 | 15 |
| 2 | ca. 520 | 6 |
| 3 | 950 | 9 |
| 4 | 1350 | 22 |
| 5 | 1800 | 27 |
| 6 | 2220 | 16 |
| 7 | 3000 | 5 |

EXAMPLE 11

Example 10 is modified: A siloxane having the structure

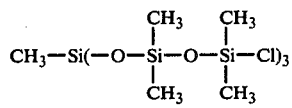

is employed in place of the tetrachloro silane. An oil having a viscosity η of 420 cP at 22° C. is obtained.

Application

An unsaturated polyester (preparation described in Example 4) is dissolved in styrene to give a 66% strength solution, the solution is stabilised with 0.01 part of hydroquinone and 0.3 part of one of the initiators of Examples 10 and 11 or benzpinacol is admixed in each case. The curing time $t_c$ and the peak temperatures (Tm) are determined analogously to Example 4.

| Bath temperature ° C. | Initiator of Example 10 | | Initiator of Example 11 | | benzpinacol | |
|---|---|---|---|---|---|---|
| | tc | Tm | tc | Tm | tc | Tm |
| 110 | 6,5 | 250 | 5,6 | 240 | 7,5 | 240 |
| 120 | 3,6 | 250 | 3,9 | 250 | 4,5 | 250 |
| 130 | 2,6 | 250 | 3,0 | 250 | 3,6 | 250 |
| 140 | 2,1 | 250 | 2,4 | 250 | 3,2 | 250 |

We claim:

1. A process for the preparation of a reaction mixture suitable as an initiator for free radical-initiated polymerisation reactions, which comprises reacting 1 mol of an α-arylketone or of an arylaldehyde of the general formula V or VI respectively $$R^4-\underset{O}{\underset{\|}{C}}-R^6 \quad (V) \qquad R^4-CHO \quad (VI)$$

wherein $R^4$ represents an aryl radical optionally substituted by $C_1$-$C_4$ alkyl, methoxy, chlorine or fluorine, and $R_6$ represents an aryl radical optionally substituted by $C_1$-$C_4$ alkyl, methoxy, chlorine or fluorine, or a $C_1$-$C_6$-alkyl radical optionally substituted by $C_1$-$C_4$ alkyl, methoxy, chlorine or fluorine, or a $C_5$-$C_7$-cycloalkyl radical or hydrogen, and approximately the equivalent amount of a base metal in an inert aprotic solvent at −10 to +70° C. with 0.4 to 0.8 mol of a dichloroorganosilane of the general formula VII $$R^1R^{2'}SiCl_2 \qquad (VII)$$

or with 0.25 to 0.6 mol of a trichloro-organosilane of the general formula VIII $$R^1 \text{SiCl}_3 \quad \text{(VIII)}$$

wherein $R^1$ represents a methyl, ethyl, phenyl, benzyl or chloromethyl radical, and $R^2$ represents a chlorine atom, a hydroxyl, methoxy, or ethoxy radical, or one of the substituents $R^1$ or with 0.1 to 0.7 mol of tetrachlorosilane, chlorinated polyorganosilanes or -siloxanes having a molecular weight of 150 to 3.000 until the exothermic reaction has ended, hydrolysing the reaction product, separating off the organic phase and stripping off the solvent under a pressure of between 2 and 6 mm Hg.

2. Reaction mixtures producible by a process as claimed in claim 1.

3. Oligomeric silyl ethers with a molecular weight, determined as a number-average, of 500 to 5,000 of the general formula I

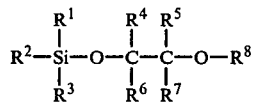

wherein
- $R^1$ denotes a methyl, ethyl, phenyl, benzyl or chloromethyl radical,
- $R^2$ denotes a chlorine atom, a hydroxyl, methoxy or ethoxy radical, $R^1$ or A,
- $R^3$ denotes a chlorine atom, a hydroxyl radical or A,
- $R^4$ and $R^5$ each denote an aryl radical optionally substituted by $C_1$–$C_4$-alkyl, methoxy, chlorine or fluorine,
- $R^6$ and $R^7$ each denote either $R^4$ or $R^5$ or an alkyl radical with 1–6 C-atoms which is optionally substituted by $C_1$–$C_4$-alkyl, methoxy, chlorine or fluorine, or a cycloalkyl radical with 5–7 C. atoms or hydrogen,
- $R^8$ denotes hydrogen or a silyl radical of the general formula II

and a denotes a radical of the general formula III

the compounds of the general formula I containing one to twenty partial structures IV

* * * * *